(12) United States Patent
Armstrong et al.

(10) Patent No.: US 7,572,635 B2
(45) Date of Patent: Aug. 11, 2009

(54) METHOD FOR AGROBACTERIUM TRANSFORMATION FOR DIHAPLOID CORN PLANTS

(75) Inventors: Charles L. Armstrong, St. Charles, MO (US); David R. Duncan, St. Charles, MO (US); Vladimir Sidorov, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/160,122

(22) Filed: Jun. 9, 2005

(65) Prior Publication Data

US 2005/0289673 A1    Dec. 29, 2005

Related U.S. Application Data

(60) Provisional application No. 60/521,724, filed on Jun. 25, 2004.

(51) Int. Cl.
*C12N 15/84* (2006.01)
*C12N 15/82* (2006.01)
*C12N 5/14* (2006.01)

(52) U.S. Cl. .................. 435/469; 435/468; 800/278

(58) Field of Classification Search ................. None
See application file for complete search history.

(56) References Cited

U.S. PATENT DOCUMENTS 6,316,694 B1 * 11/2001 Dormann et al. ............ 800/278

2002/0151057 A1 * 10/2002 Zheng et al. ................ 435/424
2002/0188965 A1 * 12/2002 Zhao et al. .................. 800/288
2003/0093829 A1 *  5/2003 Chen et al. .................. 800/278
2004/0210959 A1   10/2004 Armstrong et al. .......... 800/278

OTHER PUBLICATIONS

Hansen et. al., 1999, Trends in plant Science, vol. 4, pp. 226-231.*
Zhao et al. 2001 Molecular Breeding 8:323-333.*
Sangwan et al. 1993 Plant Science 95:99-115.*
Birchler, Practical Aspects of Haploid Production, *The Maize Handbook*, M. Freeling, V. Walbot, eds., Springer-Verlag, New York, Inc. (1994).
Cheng et al., Invited Review: Factors Influencing *Agrobacterium*-Mediated Transformation of Monocotyledonous Species, In Vitro Cell. Dev. Biol.-Plant 40:31-45 (2004).
International Search Report from PCT/US2005/020520 dated Oct. 26, 2005.
Sangwan et al., *Agrobacterium*-mediated transformation of pollen embryos in *Datura innoxia* and *Nicotiana tabacum*: production of transgenic haploid and fertile homozygous Dihaploid Plants, *Plant Science 95*:99-115 (1993).

* cited by examiner

*Primary Examiner*—Elizabeth F McElwain
*Assistant Examiner*—Li Zheng
(74) *Attorney, Agent, or Firm*—Thomas P. McBride, Esq.; Sonnenschein Nath & Rosenthal LLP

(57) ABSTRACT

The present invention relates to a novel system for generating transformed dihaploid plants from haploid cells and tissues without the use of chromosome doubling agents.

5 Claims, 3 Drawing Sheets

METHOD FOR AGROBACTERIUM TRANSFORMATION FOR DIHAPLOID CORN PLANTS

This application claims priority to U.S. provisional application Ser. No. 60/521,724 filed Jun. 25, 2004, herein incorporated by reference in its entirety.

The present invention relates to the field of plant biotechnology. In particular, provided herein are novel methods for producing transformed or transgenic plant cells and tissues, and plants. The present invention also includes the cells, tissues, and plants produced by these methods, as well as progeny and seed obtained from such plants. In some particular embodiments, corn cells, tissues, and plants are used in the invention.

Researchers have been challenged for over 50 years to develop a system for producing corn haploids routinely and at usable frequencies. Doubling of haploids provides a fully homozygous inbred in one generation, rather than having to cross and/or self-cross the plants through traditional breeding techniques involving many generations. For example, the indeterminate gametophyte (ig) genotype has been used to produce androgenetic haploids. Anther and microspore culture have been utilized extensively. Unfortunately, anther and microspore culture are time-consuming and highly genotype dependent. Wide hybridization crosses also have been used with some success in several cereal crops, but have not been successful with corn. The development of maize stock 6 into Krasnodar Haploid Inducer (KHI) reportedly allows the induction of maternal haploids in many genotypes (Birchler, James A., In: Maize Handbook, Freeling & Walbot (eds) pp. 386-388, 1994).

Transgenic inbred plants may be obtained much more quickly than the methods described above by characterizing haploids at earlier stages of plant transformation and regeneration, and then inducing diploid formation at these earlier stages. In this manner, inbreds may be obtained and analyzed much more quickly than can be achieved by methods known in the art. For example, inbreds that are homozygous for a transgene may provide an early identification of gene silencing problems in the homozygous state. These transgenic inbreds allow hybrids to be obtained with the need for an additional generation of plant growth and breeding. Additionally, costs of analyzing the plants, caring for the plants, and ultimately fixing a transgene in a population are significantly reduced.

The advantages of haploid technology also include the ability to (1) self-pollinate the R0 haploid plants; (2) avoid unnecessary steps to remove a selectable marker (e.g., typically inserted during transformation to select positively transformed tissue); (3) transform and/or regenerate plant cells, tissues, and plants without using a selectable marker; and/or (4) avoid deleterious somaclonal variations which often occur during culturing of cells and tissues and plant regeneration.

Past efforts to produce dihaploid plants from haploid tissues have required exposing the haploids to a chromosome doubling agent (such as colchicine, pronamide, APM (amiprophos-methyl, or nitrous oxide). These agents tend to be extremely toxic because they are antimicrotubule agents, thus creating numerous unwanted side-effects to the plants and serious safety considerations for those handling the agents. The present invention overcomes these deficiencies in the art, by providing a method for producing dihaploid cells, tissues, and plants without the use of a chromosome doubling agent. In particular, the method allows for diploid plant cells, tissues, and plants to be produced by transforming haploid plant cells, tissues, or plants without using a chemical chromosome doubling agent to convert the haploid to a diploid. The method is generally applicable for the production of any plant cells, tissues or intact plants, as described below. In one embodiment, exemplified herein, corn cells, tissues, and plants are utilized and produced in the methods. Although any known transformation techniques may be utilized in the invention, in some embodiments, the haploid cell, tissue or plant is transformed via host cell-mediated transformation, such as *Rhizobium* or *Agrobacterium*.

The current invention describes the identification of haploids, amplification and transformation of confirmed haploid callus (e.g., via *Agrobacterium*-mediated transformation), and regeneration of dihaploid plants. The present invention also provides transgenic corn plants made according to these methods. In invention also includes stably transformed plants, gametes, as well as offspring and seeds from any of these plants.

SUMMARY OF THE INVENTION

The present invention provides novel methods for the production of transformed dihaploid plant cells, tissues, and plants. In some embodiments, the plant cells, tissues or plants are from corn.

In one aspect, the present invention provides a method of obtaining a transformed dihaploid plant by obtaining haploid sporophytic tissue, transforming the haploid sporophytic tissue (e.g. via *Agrobacterium*-mediated transformation), and regenerating a transformed dihaploid plant therefrom in the absence of an added chromosome doubling agent. The sporophytic tissue could be an immature embryo, a mature embryo, callus (e.g., Type I or II), a nodal section, or a meristem.

In another embodiment, the invention provides a method of obtaining a transformed dihaploid plant by obtaining haploid sporophytic tissues, transforming the haploid sporophytic tissue (e.g., via *Agrobacterium*-mediated transformation), screening the haploid tissue for transformed dihaploid tissue, and regenerating the transformed dihaploid tissue to produce a transformed dihaploid plant.

In still another embodiment the invention relates to a novel method of obtaining a transformed dihaploid plant (e.g., corn) by isolating a haploid plant tissue, producing haploid callus (e.g., Type I or II), transforming the haploid callus (e.g., via *Agrobacterium*-mediated transformation), and regenerating a transformed dihaploid plant therefrom.

Still another aspect of the present invention relates to transformed plants produced by isolating a haploid tissue (e.g., corn), producing haploid callus (e.g., Type I or II), transforming the haploid callus (e.g., via *Agrobacterium*-mediated transformation), and regenerating a transformed dihaploid plant therefrom in the absence of an added chromosome doubling agent.

Yet another aspect of the present invention relates to any seeds or progeny plants obtained from any plants produced by the methods of the present invention.

Further objects, advantages and aspects of the present invention will become apparent from the accompanying figures and description of the invention.

DETAILED DESCRIPTION

Figure 1:
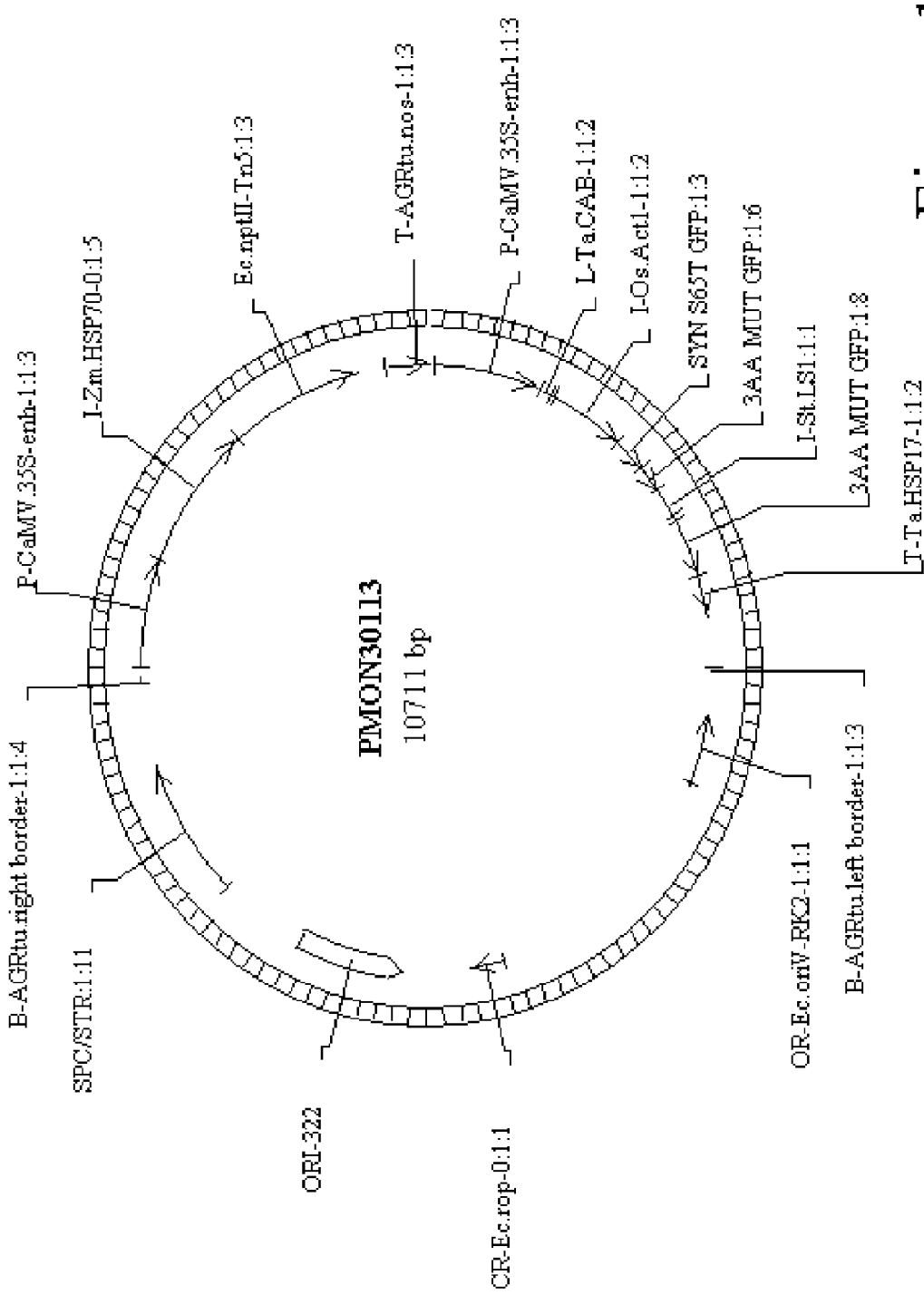
FIG. 1 is a plasmid map of pMON30113.

The following definitions will aid in the understanding of the description of the invention.

"Haploid" refers to plant cells, tissues or plants with one set (n) of chromosomes.

"Dihaploid" or "doubled haploid" refer to plant cells, tissues, or plants derived from a haploid. Dihaploids have two sets (2n) of chromosomes and are typically homozygous. It is possible, however, that mutations, deletions, or insertions, or other like modifications in the DNA may lead to some deviations from the absolute homozygosity that would normally be observed in the dihaploids. Similarly, one of skill in the art may intentionally modify the dihaploid DNA by making random or targeted mutations, deletions, insertions, or by shuffling the DNA or portions thereof. Such "modified dihaploids" are encompassed by the invention. Polyploids may also be obtained using the methods of the present invention, if desired. Polyploids will have three or more sets of chromosomes and should also be homozygous except for the modifications discussed above.

"Chromosome doubling agent" refers to a chemical that doubles the number of chromosomes in the cell (e.g., from haploid to diploid or diploid to tetraploid, etc). Such agents are typically an antimicrotubule agents such as colchicine, pronamide, or APM (amiprophos-methyl). Nitrous oxide has also been reported to be a doubling agent (US appl. 2003/0005479, incorporated by reference herein in its entirety). One of skill in the art is familiar with the compounds that can cause chromosome doubling (e.g., by blocking normal cell cycle division etc).

"Callus" refers to a dedifferentiated proliferating mass of cells or tissue.

"Type I callus" refers to callus that is morphologically compact maize callus from which whole plants can be regenerated via organogenesis, embryogenesis or a combination of the two.

"Type II callus" refers to morphologically friable, highly embryogenic maize callus (Armstrong and Green, Planta. 164:207-214. 1985).

"Seed" refers to a seed harvested from a plant; such seed may be optionally treated for storage.

"Mature embryo" refers to a zygotic embryo that can be obtained approximately 15 days or more after pollination and does not typically produce regenerable callus when cultured in vitro.

"Immature embryo" refers to a zygotic embryo that can be obtained approximately 15 days or less after pollination and can typically produce regenerable callus when cultured in vitro.

The term "zygotic embryo" is used to encompass seed, mature embryos extracted from seed, mature embryos, or immature embryos capable of germination.

"Embryogenic culture" or "embryogenic cell" or "embryogenic tissue" refers to cultured plant cells and tissues capable of being regenerated into a plant.

"Nodal section" refers to an excised portion of a germinating seedling that contains the shoot apical meristem, all subtending axillary meristems and associated leaf base tissue.

"Plant growth regulator or plant hormone" refers to compounds that affect plant growth. The plant growth regulators include, but are not limited to, auxins, cytokinins, ABA, gibberellins, ethylene, brassinosteroids, and polyamines. Auxins affect the elongation of shoots and roots at low concentration but inhibit growth at higher levels. Commonly used auxins include picloram (4-amino-3,5,6-trichloropicolinic acid), 2,4-D (2,4-dichlorophenoxyacetic acid), IAA (indole-3-acetic acid), NAA (α-naphthaleneacetic acid), and dicamba (3,6-dichloroanisic acid). Cytokinins cause cell division, cell differentiation, and shoot differentiation. Commonly used cytokinins include kinetin, BA (6-benzylaminopurine), 2-ip (2-isopentenyladenine), BAP (6-benzylaminopurine ), thidiazuron (TDZ), zeatin riboside, and zeatin.

"Coding sequence", "coding region" or "open reading frame" refers to a region of continuous sequential nucleic acid triplets encoding a protein, polypeptide, or peptide sequence.

"Endogenous" refers to materials originating from within the organism or cell.

"Exogenous" refers to materials originating from outside of the organism or cell. As used herein, exogenous is intended to refer to any nucleic acid from a source other than the recipient cell or tissue, regardless of whether a similar (but not identical) nucleic acid may already be present in the recipient cell or tissue.

"Monocot" or "monocotyledonous" refers to plants having a single cotyledon. Examples include cereals such as maize, rice, wheat, oat, and barley.

"Nucleic acid" refers to deoxyribonucleic acid (DNA) or ribonucleic acid (RNA).

"Phenotype" refers to a trait exhibited by an organism resulting from the expression (or lack of expression) of nucleic acids in the genome (including non-genomic DNA and RNA such as plasmids and artificial chromosomes) and/or organelles of the organism.

"Polyadenylation signal" or "polyA signal" refers to a nucleic acid sequence located 3' to a coding region that promotes the addition of adenylate nucleotides to the 3' end of an mRNA transcribed from the coding region.

"Promoter" or "promoter region" refers to a nucleic acid sequence, usually found 5' to a coding sequence, that alters expression of the coding sequence by providing a recognition site for RNA polymerase and/or other recognition sites for other transcription-related factors utilized to produce RNA and/or initiate transcription at the correct site on the DNA.

"Recombinant nucleic acid vector" or "vector" refers to any agent such as a plasmid, cosmid, virus, autonomously replicating sequence, phage, or linear or circular single- or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid vectors or constructs typically comprise a 5' regulatory sequence or promoter region and a coding sequence encoding for a desired gene product. The vectors are typically designed such that once delivered into a cell or tissue, the coding sequence is transcribed into mRNA, which is optionally translated into a polypeptide or protein.

"Regeneration" refers to the process of growing a plant from a plant cell or tissue.

"Selectable marker" or "screenable marker" refers to a nucleic acid sequence whose expression confers a phenotype facilitating identification of cells, tissues, or plants containing the nucleic acid sequence.

"Sporophytic" refers to plants in the phase of the life cycle that is characterized by having the double chromosome number. This is in contrast to "gametophytic", which includes microspores and anther cultures.

"Transcription" refers to the process of producing an RNA copy from a DNA template.

"Transformation" refers to a process of introducing an exogenous nucleic acid sequence into a cell or tissue. The transformation may be transient or stable. In stable transformations, part or all of the exogenous nucleic acid is incorporated (e.g., integrated or stably maintained) in the nuclear genomic DNA, plastid DNA, or is capable of autonomous replication in the nucleus or plastid.

"Transgenic" refers to organisms into which an exogenous nucleic acid sequence has been stably transformed.

The present invention can be used in dicots or monocots; preferably in monocots, and more preferably in corn. The present invention provides a method of obtaining transformed dihaploid plants, such as corn plants. In one method of the invention, haploid tissue is identified, then haploid callus is produced therefrom using routine callus induction procedures known in the art. Alternatively, callus can be produced followed by identification of haploid callus. Then, the haploid callus is transformed via *Agrobacterium*-mediated transformation to insert a gene of interest into the callus. The callus is then regenerated into a dihaploid corn plant in the absence of a chromosome doubling agent. The invention provides a transgenic dihaploid plant and a method for transformation of plant cells or tissues and recovery of the transformed cells or tissues into a differentiated dihaploid transformed plant.

The present invention was unexpected. A person of skill in this art would not anticipate that dihaploids would be produced from haploids without the use of a chromosome doubling agent. *Agrobacterium*-mediated transformation does not produce tetraploid plants from dihaploid cells that are transformed, so there was no reason to believe that it would produce dihaploid plants from haploid cells. The haploid cells are stable in culture for at least up to 12 months, so it is not a result of being in tissue culture. The spontaneous conversion rate of haploid to dihaploid in culture is about 15%. In contrast, about 50% of the haploid callus produce dihaploid plants after *Agrobacterium*-mediated transformation. Of that 50% about 36% are homozygous with the rest heterozygous. This implies that the chromosome doubling is taking place about the same time as DNA insertion.

The ability to produce dihaploid transformed plants without the use of an added chromosome doubling agent is a huge advantage. Chromosome doubling agents tend to be highly toxic chemicals because they are antimicrotubule agents. Also, when using chromosome doubling agents to produce dihaploids from haploids some tetraploids are formed as well. Also, optimization of the chromosome doubling agent is detrimental to the production of transformants in the transformation process. Ganaga & Chezhiyan (2002. Horticultural Science & Biotechnology, 77: 572-575) showed that colchicine causes problems in banana regeneration. Our own experiments have shown that even levels of colchicine below levels used for chromosome doubling greatly diminish the regenerability of plant tissues. Colchicine also injures the plant tissues genetically as exemplified by cell size and plastid number differences (Hassan & Wazuddin, 2000, Plant Breeding, 1I19: 531-533) or appearance of mutations (Ramulu, 1975; Z. pflanzenzuchtg., 74: 1-17; Guseinova, Chemically induced mutations in cotton. (Dep. 1756-79): 9pp. 1979; Neubauer & Thomas, 1966, Crop Science, 6: 209-210).

Some genetic stocks, when crossed as male onto a wide range of corn germplasm, induce a high frequency of maternal haploids. An example of such a genetic stock is Stock6 developed by the Krasnodar Institute in Russia (KHI1). In addition to a high rate of maternal haploid induction, KHI1 also conditions strong anthocyanin pigmentation in the aleurone tissue in the crown region of the kernel and in the embryo. This visible marker can be used to identify the maternal haploids. The maternal haploid kernels possess colored crowns due to normal fertilization and development of the endosperm, but colorless embryos, if the female parent is non-pigmented (Birchler, 1994. In: Maize Handbook, Freeling & Walbot (eds) pp. 386-388; Chang, 1992. Maize Genetics Newsletter, 66: 163-164).

The corn line pollinated by KHI1 will have a low percentage (5 to 10%) of its kernels being haploid. These pollinated ears can be harvested approximately 9 to 12 days post pollination, when the immature embryos are 1.5 to 2.0 mm in length and cultured on a variety of corn callus induction media known to the art (for example D medium, as described in Duncan et al., Planta 165:322-332, 1985) to produce regenerable corn callus. The haploid and diploid embryos isolated for callus induction will differ in their size, with haploid immature embryos being significantly smaller than diploid embryos. There is a considerable natural variation in embryo size on the same ear. Therefore, immature embryo size comparisons are most useful from the kernels in the same vicinity on an ear. Callus derived from these small embryos can be verified to be haploid by flow cytometric methods such as that outlined by Arumuganathan & Earle (Plant Molecular Biology Reporter. 9:229-233, 1991).

Producing haploid callus from immature embryos can be a difficult task because only a small percentage of the harvested ear will be haploid and screening by flow cytometry and other methods known to one of skill in the art can be time consuming. One efficient means to produce haploid callus is to use seedlings from seeds that are treated so as to be color marked, making the identification of the haploids easier to accomplish.

An efficient identification of corn haploid immature embryos, and callus derived from them, can be achieved by using the negative selectable marker gene pehA (phosphonate monoesterase). Such negative selectable markers may be introduced within the T-DNA of a vector used for host-cell mediated transformation, or may be introduced outside the T-DNA borders on such vectors. Cells that express the pehA gene convert the non-toxic glycerol glyphosate to toxic glyphosate and subsequently die. It is understood, however, that other negative selectable marker genes such as cytosine deaminase (which converts 5-fluorocytosine to 5-fluorouracil, which is toxic to cell growth [Plant Cell Reports 2001; 20:738-743]) may also be used equally effectively. Other selectable marker genes are readily known and available by those of skill in the art.

Inbred lines selected for the production of haploid immature embryos or callus can be pollinated with KHI that has been transformed with, and is homozygous for, the selectable marker gene pehA. After culturing on media containing glyceryl glyphosate, diploid (pehA containing) explants fail to grow, whereas maternal haploid explants produce callus typical of the maternal inbred.

Alternatively to the use of glycerol glyphosate, embryos or callus can be visually screened for pehA by using the XPP (5-bromo-4-chloro-indolyl phenylphosphonate) assay. Phosphonate monoesterase converts the XPP to a dark blue color, indicating the presence of the expressing pehA gene. This destructive assay allows for the rapid determination of pehA expression. The use of glycerol glyphosate requires time for the death of cells due to the presence of phosphonate monoesterase generated glyphosate.

Once the haploid mature corn seed is identified, it is then germinated in a media containing growth hormones. A mixture of an auxin and a cytokinin may be used. Auxins or cytokinins alone appear to give some effect, but the combination may be more effective in producing embryogenic callus. Auxins affect the elongation of shoots and roots at low concentration but generally inhibit growth at higher levels. Commonly used auxins include picloram (4-amino-3,5,6- trichloropicolinic acid), 2,4-D (2,4-dichlorophenoxyacetic acid), IAA (indole-3-acetic acid), NAA (α-naphthaleneacetic acid), and dicamba (3,6-dichloroanisic acid). Cytokinins cause cell division, cell differentiation, and shoot differentiation. Commonly used cytokinins include kinetin, BA (6-benzylaminopurine), 2-ip (2-isopentenyladenine), BAP (6-benzylaminopurine), thidiazuron (TDZ), zeatin riboside, and zeatin. One of skill in the art could easily test combinations of auxins and cytokinins to arrive at alternative combinations. In the present invention, picloram and BAP are exemplified due to their cost and performance. Also, 2,4-D is an attractive auxin based on cost. The concentration of picloram could be from about 0.5 mg/L to about 20 mg/L or from about 1 mg/L to about 15 mg/L or from about 1 mg/L to about 10 mg/L. The concentration of BAP could be from about 0.1 mg/L to about 10 mg/L or from about 0.5 mg/L to about 5 mg/L or from about 1 mg/L to about 3 mg/L. Suitable concentrations for other hormones can be readily determined by those of skill in the art of transformation. Such determinations are routine optimization. The ratio of auxin to cytokinin would not be expected to be the same across different pairs of compounds because of the differing activity levels of each compound. The ratio between auxin and cytokinins (with other phytohormones) in the plant tissue is thought to determine the developmental path the plant tissue will take. The combinations of auxin and cytokinins described in this invention are particularly useful for facilitating the induction of embryogenic callus from the apical and nodal regions of seedlings. One of skill in the art could predict or experimentally determine the reasonable concentrations of auxins and cytokinins that would work in the invention based on the knowledge of the potency of each compound and by simple experimental observations.

The seeds may also be primed prior to germination. Seed priming can be done in many ways known to those of skill in the art. Typically, seeds are gas sterilized, then coated with wet clay and fungicide and incubated at about 28° C. for 2 days in the dark. Then the seeds are placed at 15° C. for 5 days in the dark, followed by 2 days at 23° C. or 28° C. in the light. The clay can be wet with water, which appears to be most efficient, or with the media used for germination. Priming promotes more uniform germination between seeds and enhances the callus induction of the isolated nodal sections.

Once the seeds have been germinated in media containing growth hormones as described above, nodal sections can be obtained for further use. At 3 days, the nodal region is large enough to excise. After 7-10 days, the seedlings are about 3-4 cm long and easily handled. The portion of the seedling containing the coleoptile node and about 2-5 mm of subtending mesocotyl tissue and 2-5 mm of leaf tissue above the shoot apical meristem (about 0.5 cm) is cut and then split longitudinally. More callus response is obtained from the tissue as the seedling ages. After approximately 30 days, there is callus on the plant itself at the nodal region.

Isolated nodal sections are then placed on callus induction media. The appropriate callus induction media will depend upon the genotype. The callus induction media that works for callus induction of immature embryos in a genotype also seems to work for pre-treated nodal sections. Any appropriate callus induction media can be used in the present invention. A portion of the induced callus will be incapable of regenerating plants, but a person skilled in the art of tissue culture can easily separate the callus types to produce a maintainable and regenerable callus useful in transformation or other tissue culture purposes (Duncan & Widholm, Plant Science, 61: 91-103, 1989).

Any of the material produced by the preceding can be used in a transformation protocol to produce transgenic plants.

In designing a vector for the transformation process, one or more genetic components are selected that will be introduced into the plant cell or tissue. Genetic components can include any nucleic acid that is introduced into a plant cell or tissue using the method according to the invention. Genetic components can include non-plant DNA, plant DNA or synthetic DNA.

In a preferred embodiment, the genetic components are incorporated into a DNA composition such as a recombinant, double-stranded plasmid or vector molecule comprising at least one or more of following types of genetic components: (a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of polyadenylated nucleotides to the 3' end of the RNA sequence.

The vector may contain a number of genetic components to facilitate transformation of the plant cell or tissue and regulate expression of the structural nucleic acid sequence. In one preferred embodiment, the genetic components are oriented so as to express a mRNA, that in an optional embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA.

Means for preparing plasmids or vectors containing the desired genetic components are well known in the art. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters would include but are not limited to the nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (e35S), the light-inducible promoter from the small subunit of ribulose bisphosphate carboxylase (ssRUBISCO, a very abundant plant polypeptide). All of these promoters have been used to create various types of DNA constructs that have been expressed in plants Promoter hybrids can also be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive as described, and temporally regulated, spatially regulated, and spatio-temporally regulated. Other promoters that are tissue-enhanced, tissue-specific, or developmentally regulated are also known in the art and envisioned to have utility in the practice of this invention.

Promoters may be obtained from a variety of sources such as plants and plant DNA viruses and include, but are not limited to, the CaMV35S and FMV35S promoters and promoters isolated from plant genes such as ssRUBISCO genes. As described below, it is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes(see, for example U.S. Pat. No. 5,362,865). Other genetic components that serve to enhance expression or affect transcription or translational of a gene are also envisioned as genetic components.

The 3' non-translated region of the chimeric constructs should contain a transcriptional terminator, or an element having equivalent function, and a polyadenylation signal that functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 0385 962).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In one preferred embodiment, the vector contains a selectable, screenable, or scoreable marker gene. These genetic components are also referred to herein as functional genetic components, as they produce a product that serves a function in the identification of a transformed plant, or a product of agronomic utility. The DNA that serves as a selection device functions in a regenerable plant tissue to produce a compound that would confer upon the plant tissue resistance to an otherwise toxic compound. A number of selectable marker genes are known in the art and can be used in the present invention. Genes of interest for use as a selectable, screenable, or scoreable marker would include but are not limited to GUS, green fluorescent protein (GFP), luciferase (LUX), antibiotics like kanamycin (Dekeyser et al., Plant Physiol., 90:217-223, 1989), and herbicides like glyphosate (Della-Cioppa et al., Bio/Technology, 5:579-584, 1987). Other selection devices can also be implemented including but not limited to tolerance to phosphinothricin, bialaphos, and positive selection mechanisms and would still fall within the scope of the present invention.

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of agronomic interest envisioned by the present invention would include but are not limited to genes for insect or pest tolerance, herbicide tolerance, genes for quality improvements such as yield, nutritional enhancements, environmental or stress tolerances, or any desirable changes in plant physiology, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech Gen. Engin. Rev., 9:207-227, 1991). The RNA could also be a catalytic RNA molecule (i.e., a ribozyme) engineered to cleave a desired endogenous mRNA product (see for example, Gibson and Shillitoe, Mol. Biotech. 7:125-137, 1997). More particularly, for a description of anti-sense regulation of gene expression in plant cells see U.S. Pat. No. 5,107,065 and for a description of gene suppression in plants by transcription of a dsRNA see U.S. Pat. No. 6,506,559, U.S. patent application Publication No. 2002/0168707 A1, and U.S. patent application Ser. Nos. 09/423,143 (see WO 98/53083), 09/127,735 (see WO 99/53050) and 09/084,942 (see WO 99/61631), all of which are incorporated herein by reference. Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

The technologies for the introduction of DNA into cells are well known to those of skill in the art and can be divided into categories including but not limited to: (1) chemical methods; (2) physical methods such as microinjection, electroporation, and the gene gun; (3) viral vectors;(4) receptor-mediated mechanisms; and (5) Host cell-mediated plant transformation methods (e.g., *Agrobacterium* or *Rhizobium*).

Host cell-mediated transformation is achieved through the use of a genetically engineered soil bacterium belonging to the genus *Rhizobium* or *Agrobacterium*. Several such species mediate the transfer of a specific DNA known as "T-DNA", that can be genetically engineered to carry any desired piece of DNA into many plant species. The major events marking the process of T-DNA mediated pathogenesis are induction of virulence genes, and processing and transfer of T-DNA.

For *Agrobacterium*-mediated transformation, after the construction of the plant transformation vector or construct, said nucleic acid molecule, prepared as a DNA composition in vitro, is introduced into a suitable host such as *E coli* and mated into another suitable host such as *Agrobacterium*, or directly transformed into competent *Agrobacterium*. These techniques are well-known to those of skill in the art and have been described for a number of plant systems including corn, soybean, canola, cotton, and wheat.

The present invention encompasses the use of bacterial strains to introduce one or more genetic components into plants. Those of skill in the art would recognize the utility of *Agrobacterium*-mediated transformation methods. A number of wild-type and disarmed strains of *Agrobacterium tumefaciens* and *rhizogenes* harboring Ti or Ri plasmids can be used for gene transfer into plants. Preferably, the hosts contain disarmed Ti and Ri plasmids that do not contain the oncogenes that cause tumorigenesis or rhizogenesis, which are used as the vectors and contain the genes of interest that are subsequently introduced into plants. Preferred strains would include but are not limited to *Agrobacterium tumefaciens* strain C58, a nopaline-type strain that is used to mediate the transfer of DNA into a plant cell, octopine-type strains such as LBA4404or succinamopine-type strains, e.g., EHA101 or EHA105. The use of these strains for plant transformation has been reported and the methods are familiar to those of skill in the art.

The explants can be from a single genotype or from a combination of genotypes. Any corn seed that can germinate is a viable starting material. In a preferred embodiment, superior explants from plant hybrids can be used as explants. For example, a fast-growing cell line with a high culture response (higher frequency of embryogenic callus formation, growth rate, plant regeneration frequency, etc.) can be generated using hybrid embryos containing several genotypes. In a preferred embodiment an F1 hybrid or first generation offspring of cross-breeding can be used as a donor plant and crossed with another genotype. Those of skill in the art are aware that heterosis, also referred to herein as "hybrid vigor", occurs when two inbreds are crossed. The present invention thus encompasses the use of an explant resulting from a three-way or "triple hybrid" cross, wherein at least one or more of the inbreds is highly regenerable and transformable, and the transformation and regeneration frequency of the triple hybrid explant exceeds the frequencies of the inbreds individually. Other tissues are also envisioned to have utility in the practice of the present invention.

Any suitable plant culture medium can be used. Examples of suitable media would include but are not limited to MS-based media (Murashige and Skoog, Physiol. Plant, 15:473-497, 1962) or N6-based media(Chu et al., Scientia Sinica 18:659, 1975) supplemented with additional plant growth regulators including but not limited to auxins such as picloram (4-amino-3,5,6-trichloropicolinic acid), 2,4-D (2,4-dichlorophenoxyacetic acid) and dicamba (3,6-dichloroanisic acid); cytokinins such as BAP (6-benzylaminopurine) and kinetin; ABA; and gibberellins. Other media additives can include but are not limited to amino acids, macroelements, iron, microelements, inositol, vitamins and organics, carbohydrates, undefined media components such as casein hydrolysates, with or without an appropriate gelling agent such as a form of agar, such as a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Murashige and Skoog, Physiol. Plant, 15:473-497, 1962), N6 (Chu et al., Scientia Sinica 18:659, 1975), Linsmaier and Skoog (Linsmaier and Skoog, Physio. Plant., 18: 100, 1965), Uchimiya and Murashige (Uchimiya and Murashige, Plant Physiol. 15:473, 1962), Gamborg's media (Gamborg et al., Exp. Cell Res., 50:151, 1968), D medium (Duncan et al., Planta, 165:322-332, 1985), McCown's Woody plant media (McCown and Lloyd, Hort-Science 16:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures that can be optimized for the particular variety of interest.

Once the transformable plant tissue is isolated or developed in tissue culture, the next step of the method is introducing the genetic components into the plant tissue. This process is also referred to herein as "transformation." The plant cells are transformed and optionally subject to a selection step. The independent transformants are referred to as transgenic events. A number of methods have been reported and can be used to insert genetic components into transformable plant tissue.

Those of skill in the art are aware of the typical steps in the plant transformation process. The *Agrobacterium* can be prepared either by inoculating a liquid such as Luria Burtani (LB) media directly from a glycerol or streaking the *Agrobacterium* onto a solidified media from a glycerol, allowing the bacteria to grow under the appropriate selective conditions. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and therefore optimization of these parameters for any transformation method is expected.

The next stage of the transformation process is the inoculation. In this stage the explants and *Agrobacterium* cell suspensions are mixed together. The duration and condition of the inoculation and *Agrobacterium* cell density will vary depending on the plant transformation system.

After inoculation any excess *Agrobacterium* suspension can be removed and the *Agrobacterium* and target plant material are co-cultured. The co-culture refers to the time post-inoculation and prior to transfer to an optional delay or selection medium. Any number of plant tissue culture media can be used for the co-culture step. Plant tissues after inoculation with *Agrobacterium* can be cultured in a liquid or semi-solid media. The co-culture is typically performed for about one to three days.

After co-culture with *Agrobacterium*, the explants typically can optionally be placed directly onto selective media. Alternatively, after co-culture with *Agrobacterium*, the explants could be placed on media without the selective agent and subsequently placed onto selective media. Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate. Additional appropriate media components can be added to the selection or delay medium to inhibit *Agrobacterium* growth. Such media components can include, but are not limited to, antibiotics such as carbenicillin or cefotaxime.

The cultures are subsequently transferred to a media suitable for the recovery of transformed plantlets. Those of skill in the art are aware of the number of methods to recover transformed plants. A variety of media and transfer requirements can be implemented and optimized for each plant system for plant transformation and recovery of transgenic plants. Consequently, such media and culture conditions disclosed in the present invention can be modified or substituted with nutritionally equivalent components, or similar processes for selection and recovery of transgenic events, and still fall within the scope of the present invention.

The transformants produced are subsequently analyzed to determine the presence or absence of a particular nucleic acid of interest contained on the transformation vector. Molecular analyses can include but is not limited to Southern blots (Southern, Mol. Biol., 98:503-517, 1975), or PCR (polymerase chain reaction) analyses, immunodiagnostic approaches, and field evaluations. These and other well known methods can be performed to confirm the stability of the transformed plants produced by the methods disclosed. These methods are well known to those of skill in the art and have been reported (See for example, Sambrook et. al., Molecular Cloning, A Laboratory Manual, 1989). To verify that the haploid tissues were doubled, callus prior to plant regeneration or regenerated plants can be analyzed by flow cytometry, counting chloroplasts in guard cells or by rooting smears. These methods are also well known to those of skill in the art and have been reported (See for example, Burnham, In: Maize for biological research, 1982; Arumuganathan & Earle, Plant Molecular Biology Reporter, 9: 229-233, 1991; Wan et al., In Vitro Cell Dev. Biol., 28P: 87-89, 1992).

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

EXAMPLES

Example 1

Production of Haploid Seed
Haploid Embryo Induction

To produce haploid embryos for tissue culture, corn plants from inbred lines A, B, C or D were pollinated with KHI Select $C_2$ pollen in greenhouse. The immature ears were harvested 11 days after pollination. After 1 day at 4° C. in the dark, the immature embryos were removed from the kernels and plated on media 201 W (N6 salts; N6 vitamins, 1 mL/L; glycine, 1 mL/L of 2 mg/mL; 2,4-D, 1 mL/L of 1 mg/mL; casein hydrolysate, 100 mg/L; proline, 2.9 g/L; sucrose, 20 g/L; agar, 2 g/L; $AgNO_3$ 3.4 mL/L of 2 mg/mL; pH 5.8). The plates were then incubated in the dark at 28° C.

Haploid Calli Identification

Kernels with haploid embryos had normally developing endosperm (3N) and were similar to kernels with diploid embryos. Therefore, kernels with haploid and diploid embryos were indistinguishable based on their shape, size, or appearance. Haploid embryos, however, usually grew more slowly than diploid embryos. Thus haploid and diploid embryos isolated from 9- to 12-day-old (or older) were significantly smaller and could be separated from their diploid counterpart. There was considerable natural variation in embryo size on the same ear. For example, immature embryos from the top part of the ear were usually smaller than those at the bottom part of the ear. Therefore, immature embryo size comparisons were useful for the kernels in the same vicinity. Any misidentified diploid immature embryos and calli were discarded by first determining their DNA content by using flow cytometry.

Type I and type II callus from haploid immature embryos was very similar to that produced by diploid immature embryos of maternal parent (selfed ears) and visibly different from callus from F1 embryo from crosses with KHI. In addition, haploid callus, probably because of small embryo size, was initially slow growing (compared to the F1 immature embryos with KHI and diploid maternal immature embryos). After growing on 201 W media for ~13 days, callus from selfed ears was compared to callus from the ears crossed with KHI. Callus that resembled the selfed control was selected for flow cytometry analysis. For those selected, the callus was divided in half, and one piece of callus was used for flow cytometry analysis. The samples were prepared in the following manner. Callus was placed in 20/60 mm petri plate with 200 μL of PI Buffer (5 mM HEPES; 10 mM $MgSO_4*7H_2O$; 50 mM KCl; 6 mM DTT; pH 8.0; 0.25% Triton X-100) and placed on ice. Callus was not allowed to become dry. The samples were chopped vigorously with a razor for 2 minutes or until only very fine particles remained. The razor was rinsed in 800 μL of PI buffer, which was added to the plate. The samples were filtered through a 30 μm filcon filter (DAKO CN 15130) into a 1.5 mL centrifuge tube. The samples were centrifuged for five seconds at 15,000 rpm, the supernatant was pored off, and 400 μL of PI buffer with 2.4 μL of propidium iodide (5 mg/mL) was added. The samples were resuspended by vortexing gently and then incubated at 37° C. for 15 min. Samples were stored on ice in the dark until they were analyzed. The samples were analyzed using the flow cytometer (Coulter EPICS XL-MCL). Callus that was found to be haploid was transferred to fresh 201 W media and labeled as haploid.

Haploid callus can be consistently identified visually with greater than 33% accuracy using this method, as shown in Table 1. Combining this visual observation with flow cytometry was very efficient for identifying haploid lines. Table 1 shows that putative haploid IES (immature embryo scutella) and calli may be selected based on their size, callus type and morphology. With experience it should be possible to increase the frequency of identification of haploid IES and calli.

TABLE 1

Flow cytometer analysis of IES and calli selected using various criteria

| Selection criteria | Total assayed | Identified haploid | Percent haploid |
|---|---|---|---|
| IES size (A × KHI) | 31 | 12 | 38.7 |
| IES size (B × KHI) | 8 | 3 | 37.5 |
| Callus selected on type, size, morphology | 25 | 9 | 36 |
| As above, selected twice | 12 | 3 | 25 |
| Selected on callus type and size | 23 | 9 | 39.1 |
| Unselected IES | 1031 (not all assayed) | 38 | 3.7 |

Identification of haploid immature embryos and callus using negative selectable marker gene, pehA Inbred lines selected for the production of haploid immature embryos or callus were pollinated with KHI that had been transformed with, and was homozygous for, the selectable marker gene pehA. The resulting ears were harvested when their embryos were 1.25 to 2.25 mm in size. Immature embryos were plated on suitable culture media to induce the desired type of callus. The media also contained glyceryl glyphosate at levels from 0 to 5 mM to determine the appropriate selection level.

After 10 to 14 days on the callus induction medium, diploid (pehA containing) immature embryos failed to grow, whereas maternal haploid immature embryos produced callus typical of maternal inbred. These haploid calli were confirmed to be haploid by flow cytometry. Also, these haploid calli were amplified and used for transformation to produce dihaploid transgenic cultures. They may also be used to produce fully a homozygous dihaploid inbred.

Callus from crosses of corn line C×KHI/pehA and corn line A×KHI/pehA were visually screened for pehA by using XPP assays and some were found to be positive, indicating the presence of the pehA gene (Table 2). The fact that some pehA positive calli grew suggests that the glycerol glyphosate selection levels could be higher to be totally effective.

TABLE 2

Identification of haploid callus. In this table the data were accumulated for all the glyceryl glyphosate (GG) levels.

| Ear identification | XPP positive, callus growth* | XPP positive, no callus growth | XPP negative, callus growth | XPP negative, no callus growth |
|---|---|---|---|---|
| A × KHI/pehA** | 12 | 12 | 0 | 0 |
| A × KHI/pehA*** | 3 | 7 | 10 | 1 |

*Calli showed growth at 0.5, 1.0 and 1.5 mM glycerol glyphosate.
**For this ear of A × KHI/pehA, 24/24 IES/calli were XPP positive suggesting that this line may be homozygous.
***Immature ears were harvested and plated on callus induction medium with various levels of glycerol glyphosate (0, 1, 2, 3, 5 mM). Plated IES were scored for any callus growth and assayed for XPP.

Example 2

Callus Culturing

Haploid callus from corn line A was induced as described in Example 1 and grown on 201W medium (Table 3) at 28° C. in the dark, transferring to fresh media every 2 weeks.

Stability Study

Two plates each of 10 different haploid cultures were cultured separately so flow cytometry analysis could be performed over time to look for spontaneous chromosome doubling in the callus.

Two plates of 201W, each containing 0.25 g of callus, were made for each of the ten callus types. Every two weeks, a composite sample of callus (3 pieces from different parts of a plate, totaling ~100 mg) was taken from each plate for flow cytometry analysis.

When the flow cytometry samples were taken, 0.5 grams of callus from each plate was also transferred to a fresh plate of 201W to continue the stability study. This process was continued every 2 weeks for 2 months.

In the first 4 weeks of callus growth, the ratio of haploid peak to diploid peak increased significantly. In the last 2 months there was no significant change in the ratio of haploid to diploid. The ratio decreased slightly for six weeks, but increased again in the last two weeks. None of this change in ratio was outside the standard deviation. These data indicate that most haploid callus are stable for at least the first two months of growth. Further experiments demonstrated that the haploid callus was stable in culture for 6 to 12 months. After 12 months, the material is stable but not readily regenerable.

Growth Rate Study

Callus growth of 6 haploid and 5 diploid lines were compared for 2 weeks to determine whether or not they grew at comparable rates. All calli were growing in a very similar fashion prior to the study and were plated on fresh medium 4 days before the beginning of the study. From each callus line, 0.25 gram fresh weight was plated on filter paper on 201W culture medium with three replicated plates per callus line. The callus and filter paper were weighed after 6, 10, 12, and 14 days of growth.

After 2 weeks of growth, there was no significant difference between the amount of callus growth between haploid and diploid callus. The doubling time of both haploid and diploid callus lengthened with prolonged callus growth on a plate. There was also no significant difference in the doubling time of haploid and diploid callus at any period of growth.

The callus used in the growth rate study was checked for the ratio of haploid to diploid cells before and after the growth rate study. Only one plate showed a large change in the ratio of haploid to diploid, dropping from a ratio of 2.98 to 1. Otherwise, there was no significant change in the ratio of haploid to diploid peaks in the flow cytometer assay.

Example 3

Seed Germination

Seeds of haploid corn line D were kept in a desiccator for 2-24 h with sterilizing gas, which was produced by mixing of 200 mL bleach (5.25 to 6.15% sodium hypochlorite) and 2 mL HCl. (Seeds can also be sterilized in 50% bleach [bleach contains 5.25 to 6.15% sodium hypochlorite] for 20 min and washed with sterile water three times.)

For germination, the kernels were inserted with the radicle end down into the medium. For germination MSVS34 solid medium was used (Table 4) (MSVS34 medium is CM4C Basal Phytagar medium with 3 mg/L BAP, 10 mg/L picloram and 100 mg/L ascorbic acid). Seeds were incubated in 16-hour day lighting at 28° C. for 7-10 days. On MSVS34 medium, the nodal area was expanded and no roots formed at the nodal region. This area with apical and adventitious meristem usually produced the regenerable callus.

were subcultured onto fresh medium and incubated in the dark at 28° C. Calli were subcultured onto fresh medium every 3-4 weeks until enough material was produced for transformation.

TABLE 3

Media used in this invention

| Component | ½ MS VI | ½ MS FL | MS/BAP | MSOD | 609 RU | 623P | corn 65 | 201W |
|---|---|---|---|---|---|---|---|---|
| MS salts | 2.2 g/L | 2.2 g/L | 4.4 g/L | 4.4 g/L | 4.4 g/L | 4.4 g/L | — | — |
| N6 salts | — | — | — | — | — | — | 4.0 g/L | 4.0 g/L |
| Sucrose | 20 g/L | 68.5 g/L | 30 g/L | — | 20 g/L | 60 g/L | 30 g/L | 20 g/L |
| Maltose | — | — | — | 40 g/L | — | — | — | — |
| Glucose | 10 g/L | 36 g/L | — | 20 g/L | — | — | — | — |
| L-Proline | 0.115 g/L | 0.115 g/L | 1.36 g/L | — | — | — | 1.38 g/L | 2.9 g/L |
| Casamino Acids | — | — | 0.05 g/L | — | — | — | 0.1 g/L | 0.1 g/L |
| Glycine | 2 mg/L | 2 mg/L | — | — | — | — | 2 mg/L | 2 mg/L |
| L-Asparagine | — | — | — | 150 mg/L | — | — | — | — |
| myo-Inositol | 100 mg/L | 100 mg/L | — | 100 mg/L | — | 0.05 g/L | — | 90.1 mg/L |
| NicotinicAcid | 0.5 mg/L | 0.5 mg/L | 0.65 mg/L | 0.65 mg/L | — | — | 0.5 mg/L | 1.23 mg/L |
| Pyridoxine HCl | 0.5 mg/L | 0.5 mg/L | 0.125 mg/L | 0.125 mg/L | — | — | 0.5 mg/L | 1.03 mg/L |
| Thiamine HCl | 0.1 mg/L | 0.1 mg/L | 0.125 mg/L | 0.125 mg/L | — | — | 0.5 mg/L | 1.69 mg/L |
| Ca Pantothionate | — | — | 0.125 mg/L | 0.125 mg/L | — | — | — | — |
| 2,4-D | — | — | 0.5 mg/L | — | 0.2 mg/L | — | 1.0 mg/L | 1.0 mg/L |
| Picloram | — | — | 2.2 mg/L | — | — | — | — | — |
| Silver Nitrate | — | — | — | — | — | — | 3.4 mg/L | 6.4 mg/L |
| Na-Thiosulfate | — | — | — | — | — | — | — | — |
| Phytagar | — | — | 7.0 g/L | 7.0 g/L | 6.0 g/L | 6.0 g/L | 7.0 g/L | — |
| Low EEO agarose | — | — | — | — | — | — | — | 2 g/L |
| ABA | — | — | — | — | — | 0.26 mg/L | — | — |
| carbenicillin | — | — | — | — | — | 100 mg/L | — | — |
| $NaMoO_4.2H_2O$ | — | — | — | — | — | — | 1.25 mg/L | — |
| $CoCl_2.6H_2O$ | — | — | — | — | — | — | 0.125 mg/L | — |
| $CuSO_4.5H_2O$ | — | — | — | — | — | — | 0.125 mg/L | — |
| 6BA | — | — | 3.5 mg/L | — | — | — | — | — |

TABLE 4

Media for the induction of seedling-derived callus.

| Components (stock conc.) | MSV S34 | MSW57 |
|---|---|---|
| MS salts | 4.4 g | 4.4 g |
| MS vitamin 100× | 10 mL | 10 mL |
| ThiamineHCl (0.4 mg/mL) | — | 1.25 mL |
| Maltose | 40 g | — |
| Casein Hydrolysate | 0.1 g | — |
| Casamino Acids | — | 0.5 g |
| MES | 1.95 g | — |
| Magnesium Chloride | 0.75 g | — |
| Sucrose | — | 30 g |
| Glutamine | 0.5 g | — |
| L-Proline | — | 1.38 g |
| Post Autoclave additives | | |
| 2,4-D (1 mg/mL) | — | 0.5 mL |
| Picloram (1 mg/mL) | 10 mL | 2.2 mL |
| BAP (0.5 mg/mL) | 6 mL | — |
| Ascorbic Acid (50 mg/mL) | 2 mL | — |
| Silver Nitrate (2 mg/mL) | — | 1.7 mL |

Adjust pH to 5.8 before autoclaving.
Solidified with 7.0 g/L of Phytagar or 3.0 g/L Phytogel.

Example 4

Induction of Embryogenic Culture

The nodal area (~0.5 cm long) of seedlings was isolated, cut longitudinally and placed with the wounded side down on MSW57 medium (Table 4). The cultures were incubated at 28° C. with a 16-h light photoperiod. After 3-4 weeks, calli High callus induction frequency was obtained with corn line D. After one subculture, nice Type I callus was obtained. Of the available putative haploid seed, 25% was mis-identified as haploid, based on the color marker and confirmed to be diploid by flow cytometry (Table 5). Of the haploid callus produced, 80% was still haploid after six months in culture as determined by flow cytometry. The haploid callus thus maintains its ploidy over a sufficient amount of time to facilitate its transformation and the regeneration of transgenic plants.

TABLE 5

Tissue ploidy of seedling-derived callus from putative haploid seeds of corn line D.
Flow Cytometer Results*

| | Seed | | 6 month old callus | | |
|---|---|---|---|---|---|
| Ploidy | samples | % of total | samples | % of total | % of total adjusted for diploid seed |
| mixed | | | 5 | 7.35 | 9.80 |
| diploids | 6 | 25% | 22 | 32.35 | 9.80 |
| haploids | 18 | 75% | 41 | 60.29 | 80.39 |
| total | 24 | | 68 | | |

*callus analysis, based on seedlings cultured

Example 5

Bacterial Strains and Plasmids

Figure 2:
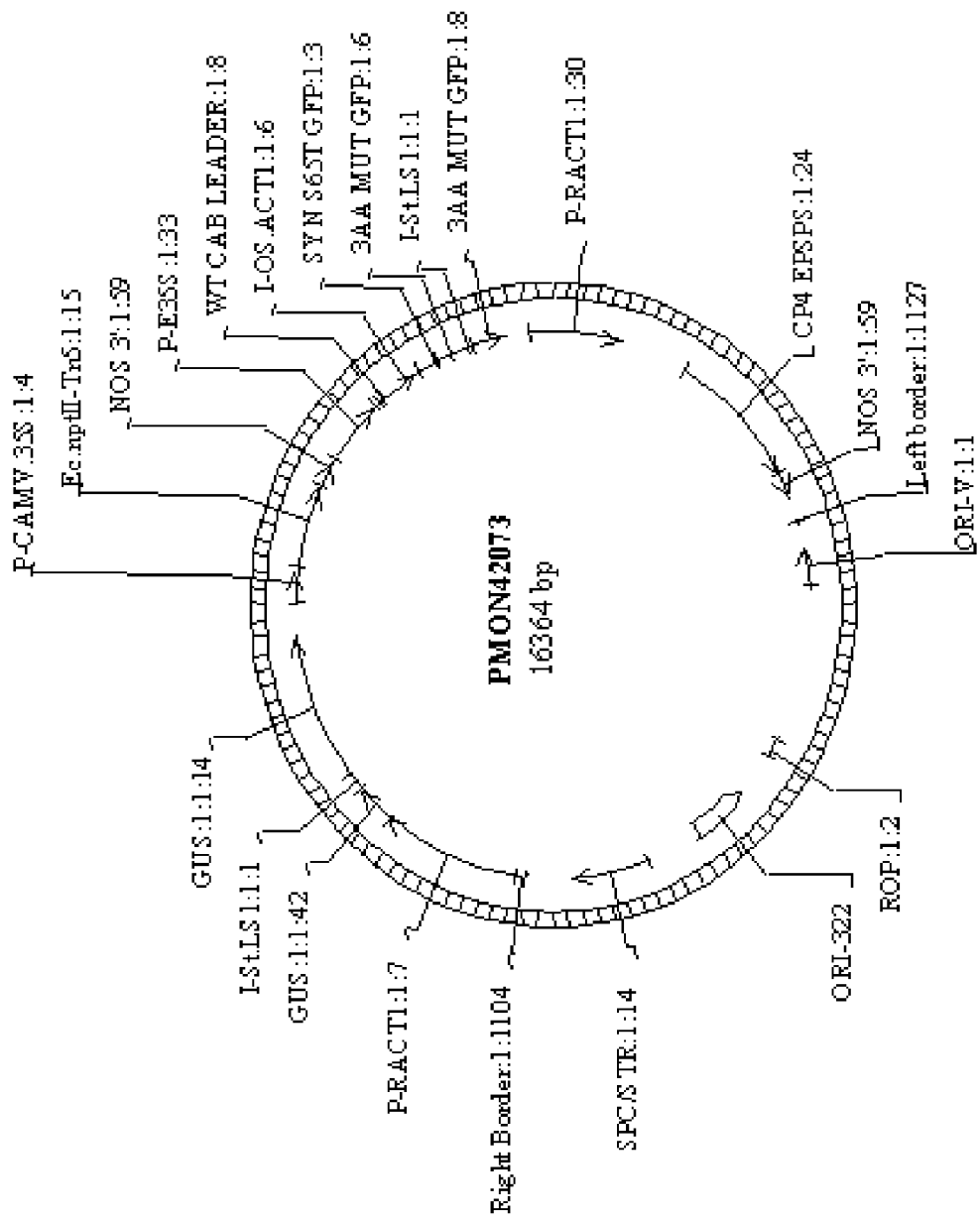
FIG. 2 is a plasmid map of pMON42073.
Figure 3:
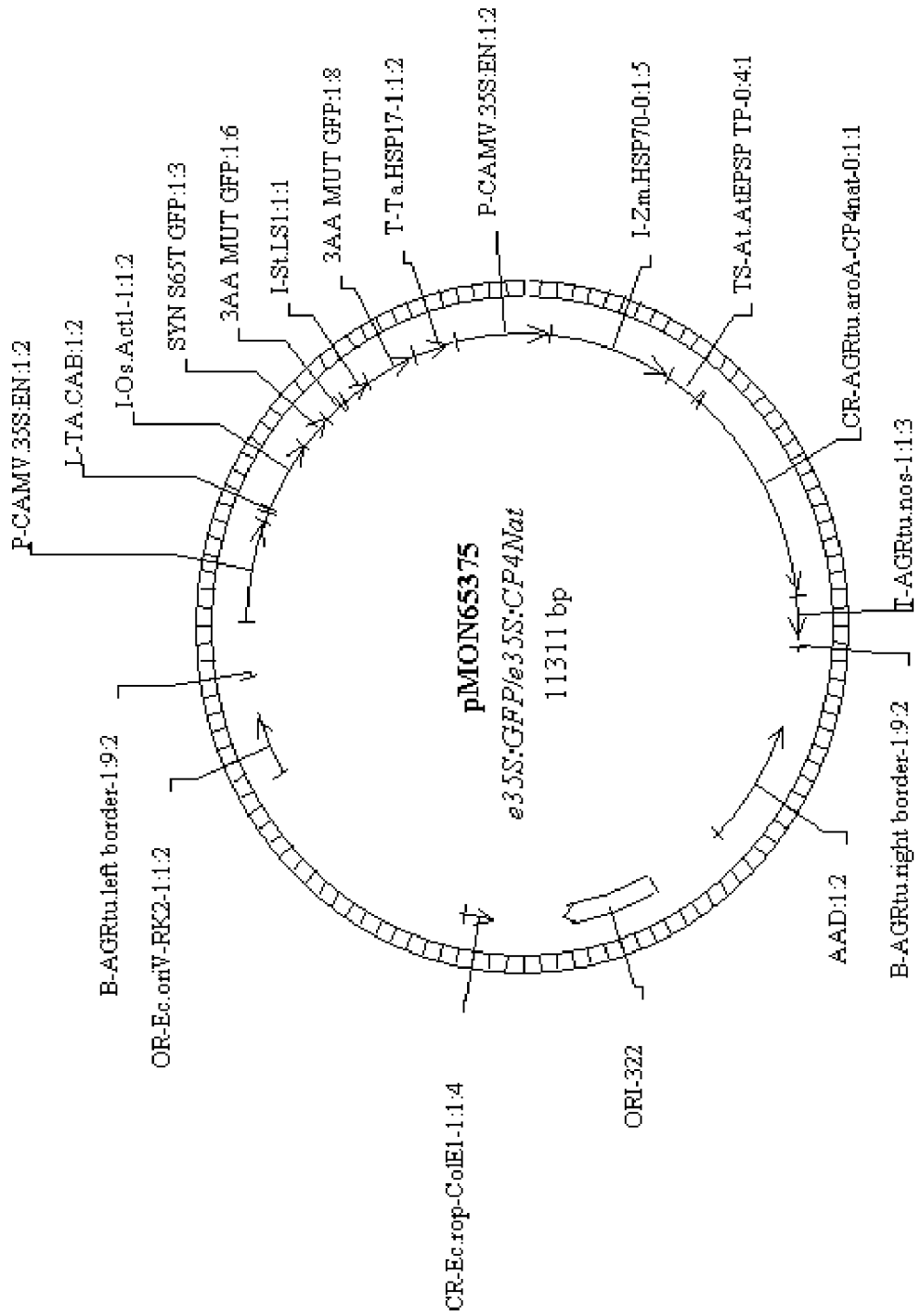
FIG. 3 is a plasmid map of pMON65375.

*Agrobacterium tumefaciens* strain ABI was harbored with a binary vector, pMON30113 (FIG. 1), pMON42073 (FIG. 2), or pMON65375 (FIG. 3). The T-DNA of the vector contained a neomycin phosphotransferase II gene (nptII) and EPSP synthase (cp4) as the selectable marker, respectively. Both plasmids contain a green fluorescence protein gene (gfp) screenable marker, both driven by 35S promoter, respectively.

Example 6

Preparation of *Agrobacterium* for Liquid Culture

Two days before the *Agrobacterium* inoculation, a loop from a freezer stock was added to 100 mL of liquid LB media with 100 mg/L spectinomycin and 50 mg/L kanamycin. This culture was grown at 200 rpm, at 28° C. in the dark until the following day. The culture was spun down at 3565 g for 15 minutes, and the supernatant was removed. The *Agrobacterium* was then resuspended in AB minimal media ($K_2HPO_4$, 3 g/L; $NaH_2PO_4$, 1 g/L; AB Salts, $NH_4Cl$, 1 g/L; $MgSO_4 \cdot 7H_2O$, 0.3 g/L; KCl, 0.15 g/L; $CaCl_2$, 0.01 g/L; $FeSO_4 \cdot 7H_2O$, 0.0025 g/L; glucose, 5 g/L; MES 4 g/L; pH 7.0) with 50 mg/L spectinomycin, 25 mg/L kanamycin, and 200 µM acetosyringone. The *Agrobacterium* was diluted to $OD_{660}$=0.2 and returned to the shaker overnight. The day of the inoculation, the *Agrobacterium* was again spun down at 3565 g for 15 minutes and then resuspended in 602 MSVI plus 200 µM acetosyringone and 20 µM silver nitrate. The *Agrobacterium* was diluted to $OD_{660}$=0.25 and placed on ice until ready to use.

Preparation of *Agrobacterium* for Solid Culture

*Agrobacterium* ABI in glycerol stock was streaked out on solid LB medium supplemented with the antibiotics kanamycin (50 mg/L), spectinomycin (100 mg/L), streptomycin (100 mg/L) and chloramphenicol (25 mg/L) and incubated at 28° C. for 2 days. Two days before *Agrobacterium* inoculation, one colony from each *Agrobacterium* plate was picked up and inoculated into 25 mL of liquid LB medium supplemented with 100 mg/L of spectinomycin and 50 mg/L of kanamycin in a 250-mL flask. The flask was placed on a shaker at approximately 150 rpm at 27° C. overnight. The *Agrobacterium* culture was then diluted (1 to 5) in the same liquid medium and put back to the shaker. Several hours later in the late afternoon one day before inoculation, the *Agrobacterium* cells were spun down at 3500 rpm for 15 min. The bacterium cell pellet was re-suspended in induction broth with 200 µM of acetosyringone and 50 mg/L spectinomycin and 25 mg/L kanamycin, and the cell density is adjusted to 0.2 at $O.D._{660}$. The bacterium cell culture (50 mL in each 250-mL flask) was then put back to the shaker and grown overnight. The following morning of inoculation day, the bacterium cells were spun down and washed with liquid ½ MSVI medium (Table 3) supplemented with 200 µM of acetosyringone. After one more spinning, the bacterium cell pellet were re-suspended in ½ MSPL medium (Table 3) with 200 µM of acetosyringone, and the cell density was adjusted to 1.0 at $O.D._{660}$ for inoculation.

Reagents were commercially available and can be purchased from a number of suppliers (see, for example Sigma Chemical Co., St. Louis, Mo.).

Example 7

*Agrobacterium*-mediated transformation

Transformation of embryogenic callus obtained from seed-derived meristem culture.

Seedling-derived embryogenic callus cultures (5-8 days after subculture to new medium) of haploid corn line D were inoculated with *Agrobacterium* prepared as described in Example 6. Individual calli that were from 3-5 mm in size were collected into an empty Petri plate. Fifteen to 20 mL of the *Agrobacterium* cell suspension were added to each plate, shaken, and set aside for 5 min. The *Agrobacterium* solution was removed with a pipette, then the calli were removed to a new plate containing Whatman #1 filter paper. The calli were then moved to a second plate containing filter paper, spread out and the plates were sealed with parafilm and left overnight in the dark. The calli were then moved to selection and regeneration as described in Example 8.

Example 8

Selection, Regeneration and Growth of Transformants with Paromomycin Selection.

After the co-cultivation, the callus pieces were transferred onto two pieces of 2 $cm^2 \times 1$ mm thick 100% acrylic felt with approximately 25 mL liquid MSW57 (Table 3) supplemented with 750 mg/L carbenicillin and 100 mg/L paromomycin in petri dishes (100 mm×25 mm) with 16 calli per plate. The plates were kept in a dark culture room at 28° C. for approximately 7-10 days after which the old medium was removed by aspiration and fresh selection medium was added to the plates. After four 10-day selection periods, on selection medium, the cultures were moved to a culture room with 16-h light/8-h dark photoperiod at 28° C. and the liquid medium was replaced with liquid MS-6BA medium (Table 3) with 100 mg/L paromomycin and 500 mg/L carbenicillin. After 7 days, the callus pieces were transferred onto the second regeneration medium, a hormone-free MS-based medium (MSOD, Table 3) with 100 mg/L paromomycin in petri dishes (100 mm×25 mm). In another 2 weeks, the callus pieces that had shoots regenerated or were still alive were transferred onto the same hormone-free medium in Phytatrays for further growth. Regenerated plants ($R_0$) when they reached to the top of Phytatrays and had one or more healthy roots were moved to soil in peat pots in a growth chamber. In 7 to 10 days, they were transplanted into 12-in pots after determining by flow cytometry that they were doubled haploids.

Glyphosate selection and regeneration on liquid medium

After the co-cultivation, the callus pieces were transferred onto two pieces of 2 $cm^2 \times 1$ mm thick 100% acrylic felt with approximately 25 mL liquid MSW57 (Table 3) supplemented with 750 mg/L carbenicillin and 0.1 mM glyphosate in petri dishes (100 mm×25 mm) with 16 calli per plate. The plates were kept in a dark culture room at 28° C. for approximately 7-10 days after which the old medium was removed by aspiration and fresh selection medium was added to the plates. After four 10-day selection periods on selection medium, the cultures were moved to a culture room with 16-h light/8-h dark photoperiod at 28° C. and the liquid medium was replaced with liquid MS-6BA medium (Table 3) with 0.25 mM glyphosate and 500 mg/L carbenicillin. After 7 days, the callus pieces were transferred onto the second regeneration medium, a hormone-free MS-based medium (MSOD, Table 3) with 0.1 mM glyphosate in petri dishes (100 mm×25 mm). In another 2 weeks, the callus pieces that had shoots regenerated or were still alive were transferred onto the same hormone-free medium in Phytatrays for further growth. Regenerated plants ($R_0$) when they reached to the top of Phytatrays and had one or more healthy roots were moved to soil in peat pots in a growth chamber. In 7 to 10 days, they were transplanted into 12-in pots after determining by flow cytometry that they were doubled haploids.

Example 9

Comparison of Doubling with and without Colchicine

Table 6 shows the results of an experiment to compare the doubling in culture, a low level of colchicine, a typical level of colchicine used for doubling, and *Agrobacterium*-mediated transformation. Approximately 16% of plants double just in the regeneration process, surprisingly about 42% of plants become diploid as a result of the transformation process. This is about a 3-fold increase in the amount of doubling. The doubling from the *Agrobacterium*-mediated transformation process is about as efficient as a very low level of colchicine (50%), but not as effective as a more typical amount (83%).

TABLE 6

Ploidy number of R0 plants treated by different process.

| Treatment | % diploid |
| --- | --- |
| no transformation + no colchicine + plant regeneration | 15.8% |
| no transformation + 0.01% colchicine + plant regeneration | 50.0% |
| no transformation + 0.025% colchicine + plant regeneration | 83.0% |
| transformation + no colchicine + plant regeneration | 41.9% |

Transgenic Plant Analyses

The plants were grown in a greenhouse under appropriate growth conditions as described above. Many of the plants were fully fertile. Each plant was examined by assessing GFP expression in pollen grains or by Southern hybridization analysis (Southern, Mol. Biol., 98:503-517, 1975). Several of the transgenic lines produced plants that shed only GFP expressing pollen, which indicated that about 36% of these plants were homozygous for the transgene (Table 7). These results were further confirmed by southern analysis.

TABLE 7

Homozygosity of pollen from transformed haploids without chromosome doubling agent.

| ZM # | Ploidy | CP4 copy # | NPTII Copy # | Homozygosity (+/−) |
| --- | --- | --- | --- | --- |
| ZM S107926 | 2n | 1 | | − |
| ZM S107930 | 2n | 1 | | − |
| ZM S107923 | 2n | 1 | | − |
| ZM S107924 | 2n | 2 | | + |
| ZM S107927 | 2n | 1 | | + |
| ZM S107955 | 2n | | 0 | + |
| ZM S107964 | ? | | 0 | − |
| ZM S107963 | 2n | | 0 | − |
| ZM S107935 | 2n | | 0 | − |
| ZM S107972 | 2n | | 1 | + |
| ZM S107990 | 2n | | 1 | + |
| ZM S107926 | 2n | | 1 | − |

TABLE 7-continued

Homozygosity of pollen from transformed haploids without chromosome doubling agent.

| ZM # | Ploidy | CP4 copy # | NPTII Copy # | Homozygosity (+/−) |
| --- | --- | --- | --- | --- |
| ZM S107995 | 2n | | 4 | − |
| % homozygous | | | | 35.7% |

What is claimed is:

1. A method of obtaining a transformed dihaploid corn plant comprising: obtaining haploid sporophytic corn tissue; transforming the haploid sporophytic tissue via *Agrobacterium* mediated transformation; and regenerating a transformed dihaploid corn plant from the transformed haploid tissue; wherein the method is conducted in the absence of an amount of a chromosome doubling agent that would cause chromosome doubling if present, and wherein transformed dihaploid plants are produced by the method in an amount increased about 3-fold relative to the method without the step of transforming the haploid sporophytic tissue.

2. The method of claim 1 in which the sporophytic tissue is immature embryo, mature embryo, callus, nodal section, or meristem.

3. A method of obtaining a transformed dihaploid corn plant comprising: obtaining haploid sporophytic corn tissue; culturing the haploid sporophytic corn tissue to form haploid corn callus; transforming the haploid corn callus via *Agrobacterium*-mediated transformation; and regenerating a transformed dihaploid corn plant from the transformed haploid corn callus in the absence of an added chromosome doubling agent, and wherein transformed dihaploid plants are produced by the method in an amount increased about 3-fold relative to the method without the step of transforming the haploid sporophytic tissue.

4. A method of obtaining a transformed dihaploid corn plant comprising: obtaining haploid sporophytic corn tissue; transforming the haploid sporophytic tissue via *Agrobacterium*-mediated transformation; screening the transformed haploid sporophytic corn tissue for transformed dihaploid tissue; and regenerating a transformed dihaploid corn plant from the transformed dihaploid tissue, wherein the method is conducted in the absence of an amount of a chromosome doubling agent that would cause chromosome doubling if present, and wherein transformed dihaploid plants are produced by the method in an amount increased about 3-fold relative to the method without the step of transforming the haploid sporophytic tissue.

5. The method of claim 1 wherein the haploid sporophytic tissue is obtained from embryos created by crossing an inbred corn line with pollen from a haploid inducing line.

* * * * *

UNITED STATES PATENT AND TRADEMARK OFFICE
CERTIFICATE OF CORRECTION

PATENT NO.       : 7,572,635 B2
APPLICATION NO.  : 11/160122
DATED            : August 11, 2009
INVENTOR(S)      : Armstrong et al.

Page 1 of 1

It is certified that error appears in the above-identified patent and that said Letters Patent is hereby corrected as shown below:

In claim 1, column 22, line 15, delete "agrobacterium mediated" and insert --agrobacterium-mediated--.

Signed and Sealed this

Twenty-seventh Day of October, 2009

David J. Kappos
*Director of the United States Patent and Trademark Office*